United States Patent [19]
Montgomery

[11] Patent Number: 6,114,646
[45] Date of Patent: Sep. 5, 2000

[54] APPARATUS AND METHOD FOR DETECTING DOCUMENTS HAVING FERROUS OBJECTS

[75] Inventor: Robert B. Montgomery, Palmyra, N.J.

[73] Assignee: Opex Corporation, Moorestown, N.J.

[21] Appl. No.: 08/989,784

[22] Filed: Dec. 12, 1997

[51] Int. Cl.[7] .............................. B07C 5/00; G01N 27/72
[52] U.S. Cl. ........................ 209/562; 209/900; 324/235; 324/243
[58] Field of Search ............................... 209/8, 226, 227, 209/900, 559, 562; 324/235, 239, 243; 235/449

[56] References Cited

U.S. PATENT DOCUMENTS

| | | | |
|---|---|---|---|
| 3,731,752 | 5/1973 | Schad | 324/247 |
| 3,878,367 | 4/1975 | Fayling et al. | 360/131 |
| 4,518,919 | 5/1985 | Ishida | 324/235 X |
| 4,863,037 | 9/1989 | Stevens et al. | 209/3.1 |
| 5,078,252 | 1/1992 | Furuya et al. | 324/243 X |
| 5,310,062 | 5/1994 | Stevens et al. | 209/584 |
| 5,397,003 | 3/1995 | Stevens et al. | 209/534 |
| 5,439,118 | 8/1995 | York | 209/900 X |
| 5,441,159 | 8/1995 | DeWitt et al. | 209/584 |
| 5,460,273 | 10/1995 | Stevens et al. | 209/577 X |

FOREIGN PATENT DOCUMENTS 4232358  4/1993  Germany ................................ 324/243

*Primary Examiner*—Tuan N. Nguyen
*Attorney, Agent, or Firm*—Stephen H. Eland; Dann, Dorfman, Herrell and Skillman

[57] ABSTRACT

A ferrous object detection circuit for use with automated document processing devices is provided for detecting and sorting documents affixed with ferrous objects such as staples and paper clips. A static magnetic field is positioned to intersect a document path. At least one inductive transducer is positioned relative to the magnetic field to detect changes in the magnetic field resulting from documents traveling along the document path. The movement of ferrous objects through the static magnetic field produces a detection signal in the inductive transducer, identifying the document as having a ferrous object.

2 Claims, 2 Drawing Sheets

APPARATUS AND METHOD FOR DETECTING DOCUMENTS HAVING FERROUS OBJECTS

FIELD OF THE INVENTION

This invention relates to the automated processing of bulk mail, including identifying documents affixed with ferrous materials such as staples and paper clips. More particularly, the present invention relates to a document processing apparatus having a magnetizing element producing a magnetic field and a sensor for detecting changes in the magnetic field in response to a document having a ferrous object.

BACKGROUND OF THE INVENTION

The timely processing of invoices and payments is an essential tool to modern business. A variety of businesses customarily receive mail in large quantities and in bulk form. A number of devices have been developed to handle bulk mail to facilitate efficient processing of the contents, so that payments can be deposited rapidly. Such devices extract the documents from the envelopes, then reorient and sort the documents. An example of a comprehensive apparatus of this general type is the Opex System 150, which is manufactured by Opex Corporation of Moorestown, N.J.

When sorting documents, it is desirable to detect documents containing ferrous objects such as staples and/or paper clips that may damage the apparatus and/or the documents if processed. Therefore, it is desirable to separately sort documents having a paper clip or staple so that the documents can be processed manually.

SUMMARY OF THE INVENTION

In light of the foregoing, the present invention provides an apparatus for processing documents to detect documents to which ferrous objects are attached. The apparatus includes a document transport for conveying a document along a document path. A magnetizing element disposed along the document path produces a magnetic field directed toward the document path. A sensor disposed along the document path positioned relative to the magnetizing element detects variations of the magnetic field to determine whether a ferrous object is connected to a document.

In addition, the present invention provides a method for processing documents to detect documents to which ferrous objects are attached. The method provides for conveying a document along a document path. A magnetic field is directed toward the document path, and changes in the magnetic field are monitored. The presence of a document having a ferrous object is then determined in response to changes in the magnetic field.

BRIEF DESCRIPTION OF THE DRAWINGS

The foregoing summary, as well as the following detailed description of the preferred embodiments of the present invention, will be better understood when read in conjunction with the accompanying drawings in which.

DETAILED DESCRIPTION OF THE PREFERRED EMBODIMENTS

Figure 1:
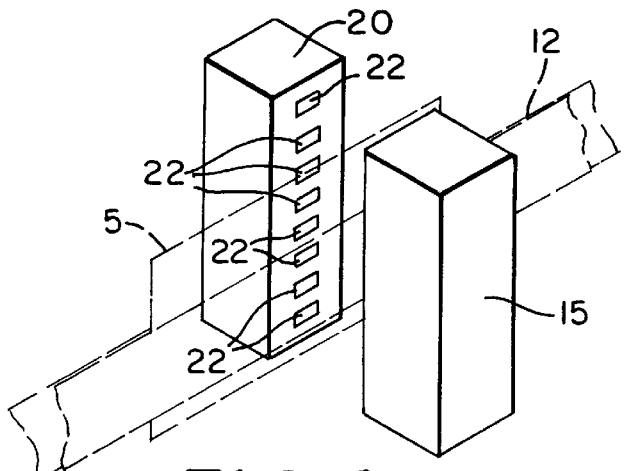
FIG. 1 is a schematic perspective view of a document processing apparatus according to the present invention.
Figure 4A:
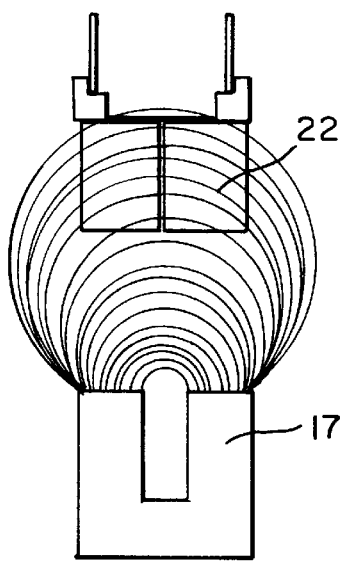
FIG. 4a is a schematic plan view of the apparatus of FIG. 1, illustrating the magnetic filed lines produced by a magnetizing element incorporated in the apparatus, shown in a absence of a ferrous object.
Figure 4B:
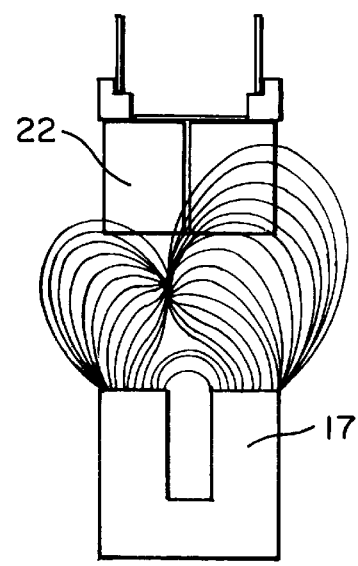
FIG. 4b is a schematic plan view of the apparatus of FIG. 4a, illustrating the magnetic field lines produced when a ferrous object is present in the magnetic filed.

Referring now to the drawings in general and to FIGS. 1, 4a, and 4b specifically, an apparatus for detecting ferrous objects on documents is designated 10. The apparatus 10 includes a magnetizing element 15 and a sensor 20 positioned along a document path 12. The magnetizing element 15 produces a magnetic field directed toward the document path. If a ferrous object such as a paper clip or staple is attached to a document, then the magnetic field fluctuates when the document is conveyed past the magnetizing element 15. The sensor 20 detects the fluctuations in the magnetic field and produces a signal indicative of a metal object. The documents are then electronically identified as having a metal object, so that the documents can be out-sorted for manual processing.

The apparatus 10 preferably is incorporated into a mail processing device that extracts documents from envelopes, and re-orients and sorts the documents, such as the system 150 produced by Opex Corporation of Moorestown N.J. Alternatively, the detection apparatus 10 can operate as a stand alone device for preprocessing documents before the documents are processed by an automated machine. In addition, the apparatus can scan documents either before or after the documents have been extracted from the envelopes. Therefore, in the description of the present invention, the term document is meant to include an envelope containing one or more documents as well as a document such as a check or invoice that is not contained within an envelope.

Referring now to FIG. 1, a conveyor comprising a pair of opposing belts conveys a document 5 along a document path 12. For clarity, the conveyor and documents 5 are shown in phantom in FIG. 1. The conveyor conveys the document between the magnetizing element 15 and the sensor 20.

The magnetizing element 15 produces a magnetic field directed toward the document path. The magnetizing element 15 preferably includes a permanent magnet 17 having a height that is greater than the height of the tallest envelope or document ordinarily processed by the apparatus. In the present instance, the magnet 17 is made of three ceramic magnet segments forming a magnet approximately 8" high. The magnet 17 produces a magnetic field that is generally static in the absence of a ferrous object passing through the magnetic field. In addition, the magnetizing element 15 produces a magnetic field that intersects the documents along the entire height of the documents as the documents are conveyed past the magnetizing element. Therefore, regardless of where a ferrous object is connected to a document, the ferrous object will pass though at least a portion of the magnetic field.

The size, type and number of magnets may be varied. Increasing the strength of the magnet increases the strength of the signal received by the sensor 20. However, increased magnet strength generally leads to increased noise detected by the sensor 20.

The sensor 20 is positioned adjacent the document path 12, opposing the magnetizing element 15 and spaced apart from the magnetizing element and the document path. The sensor 20 includes at least one read head 22. Each read head 22 is a transducer constructed of a coil bobbin and ferrite cores. The center post of the ferrite cores are gapped to control the coupling of the cores to achieve a specific and accurate inductance. A small magnetic insulating material such as plastic, brass, or aluminum is inserted between the ferrite core halves to control the gap of the core halves. The gap material provides de-coupling between ferrite cores so that the changes in the magnetic field can be detected as ferrous objects pass along document path 12. In the preferred embodiment the gap is about 0.010" inches and centrally located between the core halves.

Although a single read head 22 may be used in some applications, preferably the sensor 20 includes a plurality of read heads forming a vertical array. The read heads 22 are positioned adjacent the document path 12 opposing the magnetizing element 15 and within the static magnetic field of the magnetizing element. The read heads 22 are positioned in an array such that the gaps between the ferrite cores of the transducers are centered along a line.

In the preferred embodiment, the read heads 22 are spaced apart approximately ½ from each other. As shown in FIG. 1, the array of read heads includes eight read heads vertically spaced from one another to monitor a 7.5" scan area corresponding to the magnetic field produced by the magnet 17. Spaced in this way, the mutual coupling between the adjacent read heads 22 provides a consistent signal level along the entire length of the array. Therefore, a ferrous object passing directly between two heads yields the same detection signal it would produce if it passed directly over a single head.

Because the read heads 22 are open to the outside environment to scan the mail, there is a limit to the amount of shielding that can be provided. To compensate for the environmental noise, the coil of one of the transducers is wound in the reverse direction. Preferably the read head 22 at the top of the array has the reverse-wound coil because the top coil is ordinarily above th height of the documents. Therefore, the top read head 22 generally only monitors background or environmental noise. A uniform field striking the reverse-wound coil produces a voltage signal in the opposite direction to the rest of the array. The gain of this reverse-wound read head is adjustable from 0.9 to 10 times the gain of the rest of the array. By running the motors and measuring the amplifier output with a DVM or oscilloscope, the gain of this reverse-wound read head can be adjusted to provide a minimum signal output generated by AC devices in the target system.

Figure 2:
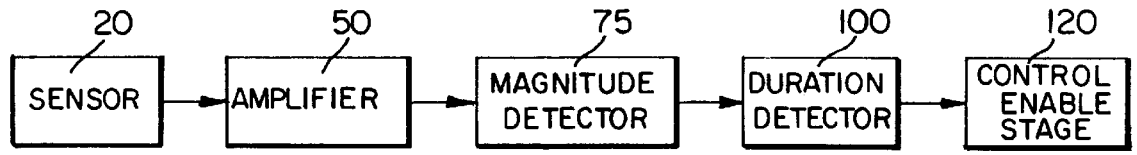
FIG. 2 is a functional block diagram of a ferrous object detection circuit incorporated in the apparatus illustrated in FIG. 1.

Referring now to FIG. 2, the operation of a ferrous object detection circuit 10 is shown in the functional block diagram. The circuit 10 includes a sensor 20, an amplifier 50, a magnitude detector 75, a duration detector 100, and a control enable stage 120.

The read heads 22 of the sensor 20 detect the presence of ferrous objects on a document 5. If a read head detects a variation in the magnetic field produced by the magnet, the read head produces a detection signal.

The amplifier 50, receives the detection signals from all of the read heads 22 and sums the detection signals. By summing the detection signals, a single signal indicative of a ferrous object is provided for further processing regardless of which read head or read heads detected the ferrous object.

The magnitude detector 75 compares the magnitude of the summed signal against a predetermined threshold. If the summed signal is above the threshold, the magnitude detector produces signal indicative of a ferrous object. If the magnitude of the summed signal is below the threshold, the magnitude detector 75 does not produce a signal indicative of a ferrous object.

The duration detector 100 distinguishes noise signals emanating from the electromechanical hardware of the document processing apparatus from detection signals. The duration detector 100 distinguishes the noise based on the duration of the signal received from the magnitude detector 75.

The control enable stage 120 interfaces with the circuitry of the document processing apparatus for producing a ferrous object identification signal.

The ferrous object detection circuit 10 is powered by 12 volt and five volt power taps of the document processing apparatus.

Figure 3:
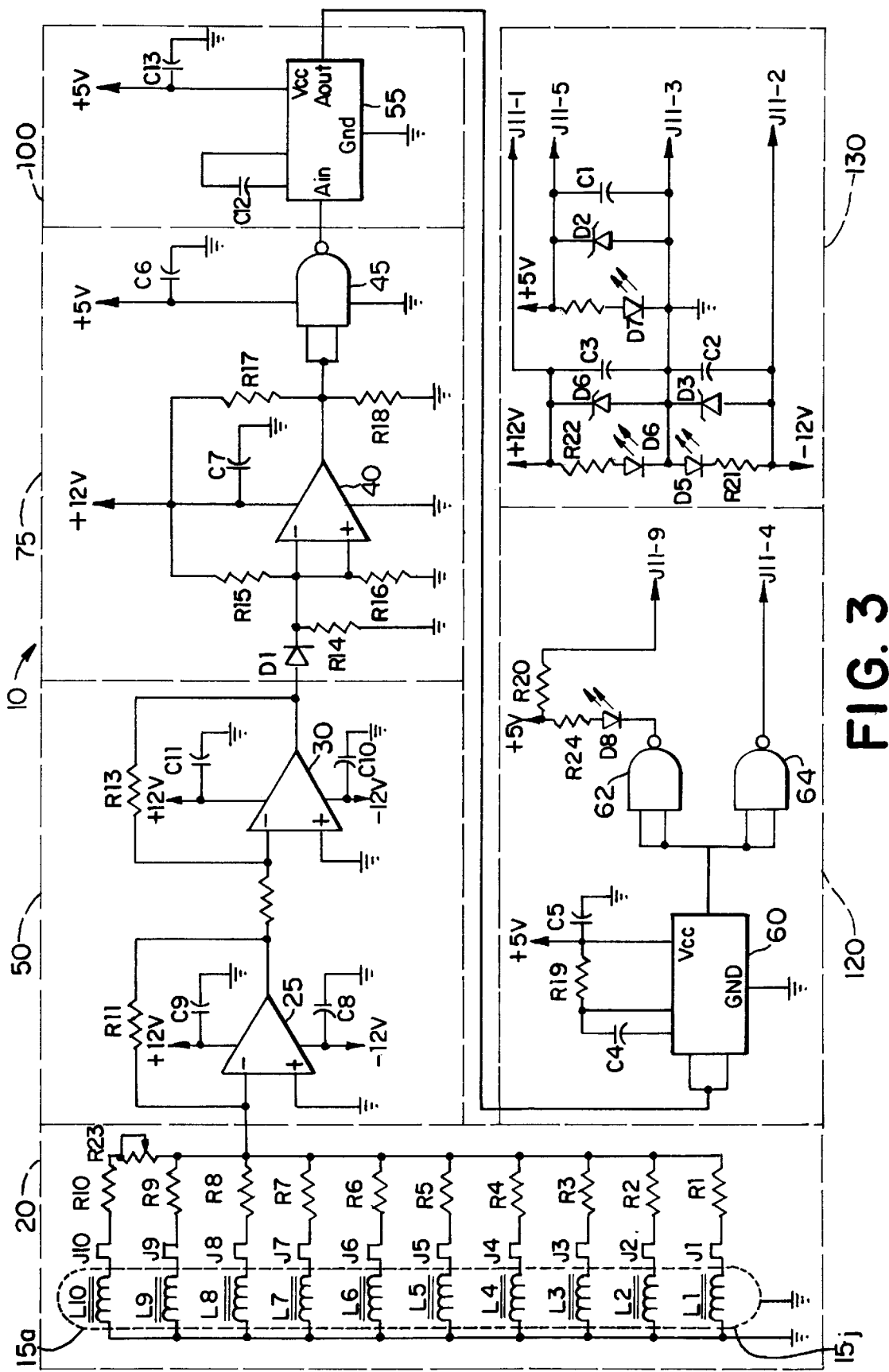
FIG. 3 is a schematic diagram of the ferrous object detection circuit.

Referring now to FIG. 3, a schematic diagram of the ferrous object detection circuit 10 is shown. The sensor 20 includes the array of read heads 22. The read heads 22 are illustrated as inductors L1–L10 at approximately 10.5 mh having terminals grounded to a DC return path and second terminals connected through jumper J1–J10 to gain resistors R1–R10. Although the circuit shows connections for ten read heads, as noted above only eight are used in the present instance. The read heads 22 are surrounded by aluminum rails. The rails are also grounded to a DC return path for reducing electrical noise. The J1–J10 are provided for insulating individual transducers for electrical set-up, testing, and troubleshooting. The gain resistors R1–R10 pass induced detection signals of sensing stage 20 to the amplifier 50.

The amplifier 50 is a two-stage amplifier including a summing amplifier 25 and a secondary amplifier 30. The amplifier 50 sums all the detection signals from the sensor 20 through the summing amplifier 25, which is preferably a Linear Technologies LT1024 dual op-amp. Each detection signal is amplified by a ratio of R11 to each individual gain resistor of sensing stage 20. Capacitors c9 and c8 provide a path to ground for supply voltage noise. Amplifier 30 further amplifies the signal of summing amplifier 25 by a ratio equivalent to R13/R12. Capacitors c10 and c11 provide a path to ground for supply voltage noise.

The amplified AC detection signal is half-wave rectified by a diode D1 of type 1N914. The positive half-cycle of the amplified detection signal is input to the magnitude detector 75.

The magnitude detector 75 includes a comparator 40, which is preferably a Texas Instruments LM339 differential comparator. The comparator threshold voltage is determined by the voltage divider formed by resistors R15 and R16. Capacitor c7 provides a path to ground for supply voltage noise. The output of the comparator for a voltage above or below the comparator threshold is determined by the voltage divider of R17 and R18. In the present instance, if the comparator detects a signal that is greater than two volts, the output of the comparator is five volts. If the comparator detects a signal that is less than two volts, the output of the comparator is zero volts.

The output of the magnitude detector 75 is received by a nand gate 45. The nand gate 45 is wired as an inverter to clean up the comparator signal, sharpening the transitions of the detection pulse for TTL processing of duration detector 100.

The duration detector 100 includes a Motorola MC14490 Hex Contact Bounce Eliminator 55. The duration detector 55 filters out detection pulses which are not present at its input for four or more consecutive clock pulses. The clock frequency is 10 Khz, as determined by capacitor c12 with four clock pulses equaling 400 $\mu$secs. A vertical staple typically provides a signal of 1 msec to 2 msec long, while false signals from DC motor brushes are typically less than 200 μsec long. Capacitor c13 provides a path to ground for supply voltage noise. In this way, if the magnitude detector 100 detects a signal that is at least 400 μsec, then the duration detector passes a control signal to the control enable stage 120.

The control enable stage 120 includes a hardware timer, preferably a Texas Instruments 74121 Monostable Multivibrator 60. The pulse width required for interface to the document processing apparatus is 25 msec. The values of c4 and R19 dictate the pulse width of the multivibrator 60 which is ≡0.7c4R19=35 msec. The output of the multivibrator 60 is provided to two Nand gates 62 and 64 wired as inverters. Gate 62 is wired to fire the diagnostic LED D8 to show triggering of the unit as ferrous objects pass along the document path 12. Gate 64 is wired to fire the LED of the opti-coupler on the control board of the document processing device. J11-9 is wired to the anode of the opti-coupler and J11-4 is wired to the cathode. R20 provides the current limit to the forward conduction of the opti-coupler LED. In this way, if the control enable stage 120 receives a control signal from the duration detector 100 indicating the presence of a ferrous object, the control enable stage stretches the signal to ensure that the control signal is at least 25 msec.

Included in FIG. 3 is operator circuit 130. Diodes D6 and D5, through current limiting resistors R22 and R21 provide visual indication to operators that 12 volt circuit potential is present. D7, through current limiting resistor R23 provides visual indication to operators that 5 volt circuit potential is present.

The terms and expressions which have been employed are used as terms of description and not of limitation. There is no intention in the use of such terms and expressions of excluding any equivalents of the features shown and described or portions thereof. It is recognized, however, that various modifications are possible within the scope of the invention as claimed. For example, the duration detector 100 stage may be comprised of a number of discrete components such as appropriately configured latches. Similarly a number of components may be consolidated and described in terms of a single dedicated specifically programmed hardware module utilized solely for performing circuit stage functions.

That which is claimed is:

1. An apparatus for processing documents, comprising:
   a document transport for conveying a document along a document path;
   a magnetizing element disposed along the document path producing a magnetic field directed toward the document path;
   a plurality of read heads disposed along the document path, vertically spaced from one another, opposing the magnetizing element, wherein each read head detects at least a portion of the magnetic field and produces a detection signal in response to a variation in the portion of the magnetic field associated with the read head;
   a summing element for summing the signals received from the read heads for the document to produce a summed signal;
   an amplifier for amplifying the summed signal; and
   a detector for receiving the summed signal to produce an output signal indicative of a ferrous object on the document, wherein the detector includes:
      a filter for eliminating signals having a magnitude below a predetermined threshold; and
      a signal duration detector operable to eliminate signals having a signal duration shorter than a predetermined duration.

2. The apparatus of claim 1 comprising a compensation read head operable to detect at least a portion of the magnetic field and produce a compensation signal opposing the detection signal in response to a variation in the portion of the magnetic field associated with the compensation read head wherein the summing element sums the signals received from the read heads and the compensation read head to produce a summed signal.

* * * * *